US006372728B1
:::

(12) United States Patent
Ungell

(10) Patent No.: US 6,372,728 B1
(45) Date of Patent: Apr. 16, 2002

(54) FORMULATION FOR TREATMENT OF OSTEOPOROSIS

(75) Inventor: Anna-Lena Ungell, Västra Frölunda (SE)

(73) Assignee: AstraZeneca AB, Sodertalje (SE)

( * ) Notice: Subject to any disclaimer, the term of this patent is extended or adjusted under 35 U.S.C. 154(b) by 0 days.

(21) Appl. No.: 09/171,950

(22) PCT Filed: Oct. 5, 1998

(86) PCT No.: PCT/SE98/01790

§ 371 Date: Oct. 29, 1998

§ 102(e) Date: Oct. 29, 1998

(87) PCT Pub. No.: WO99/18972

PCT Pub. Date: Apr. 22, 1999

(30) Foreign Application Priority Data

Oct. 10, 1997 (SE) .............................................. 9703691

(51) Int. Cl.⁷ .............................................. A61K 31/66
(52) U.S. Cl. ...................................................... 514/109
(58) Field of Search ................................. 514/108, 109

(56) References Cited

U.S. PATENT DOCUMENTS

| | | | | |
|---|---|---|---|---|
| 5,133,972 A | * | 7/1992 | Ferrini et al. ................ | 424/449 |
| 5,391,743 A | * | 2/1995 | Ebetino et al. ................ | 546/22 |
| 5,958,908 A | * | 9/1999 | Dohi et al. ................... | 514/108 |

FOREIGN PATENT DOCUMENTS

| | | |
|---|---|---|
| WO | 9205771 | 4/1992 |
| WO | 9419003 | 9/1994 |

OTHER PUBLICATIONS van Hoogdalem et al. "Intestinal Drug Absorption Enhancement: An Overview." Pharmac. Ther. 44:407–443, 1989.

Swenson et al. "Means to Enhance Penetration: Intestinal Permeability Enhancement . . . " Adv. Drug Deliv. Reviews 8:39–92, 1992.

Sato et al. Bisphosphonate Action. (1991) J. Clin. Invest. 88,2095–2105.

Lin, J.H., Bisphosphonates: A Review of their Pharmacokinetic Properties. Bone 18:75–85, 1996.

Fleisch, H. Bisphosphonates in bone disease, Stampli & Co., Bern (1993) p. 50–54.

Gertz et al. Studies of the oral bioavailability of Alendronate. Clinical Pharmacology & Therapeutics, 58:288–298, 1995.

Muranishi, S. Absorption Enhancers. Crit. Rev. Ther. Drug Carrier Syst. 7:1–33 (1990).

Sekine et al. Improvement of Bioavaliability of Poorly Absorbed Drugs . . . (1985) J. Pharmacobio–Dyn 8:286–295.

Beskid et al. (1988) enteral, Oral, and Rectal Absorption of Ceftriaxone Using Glyceride Enhacers. Chemotherapy 34, 77–84.

Matsumoto et al. Enhancing Effects of Glyceryl–1–monooctanoate on Rectal Absorption . . . (1989), Chem. Pharm. Bull. 37:2477–2480.

Constantinides et al. (1995) Lipid Microemulsion for Improving Drug Dissolution and Oral Absorption: Physical and Biopharmaceutical Aspects 12:1561–1572.

Fleisch, H. Bisphosphonates: A New Class of Drugs in Diseases of Bone and Calcium Metabolism. Recent Results Cancer Res. 116:1–28 (1989).

Drug Absorption Enhancement (ed.: A B G de Boer), Harwood Academic Pub., 1994, p. 155–175.

* cited by examiner

Primary Examiner—Theodore J. Criares
(74) Attorney, Agent, or Firm—White & Case LLP

(57) ABSTRACT

The present invention provides pharmaceutical formulations comprising at least one bisphosphonate and an absorption enhancing agent essentially consisting of a medium chain glyceride or a mixture of medium chain glycerides. The said pharmaceutical formulations are useful for the inhibition of bone resorption and for the treatment and prevention of osteoporosis.

29 Claims, 1 Drawing Sheet

FORMULATION FOR TREATMENT OF OSTEOPOROSIS

TECHNICAL FIELD

The present invention relates to pharmaceutical formulations comprising bisphosphonates. The invention also relates to a process for preparing such pharmaceutical formulations, to the use of such pharmaceutical formulations for inhibition of bone resorption and for the treatment and prevention of osteoporosis.

BACKGROUND ART

Bisphosphonates

Bisphosphonates are carbon-substituted pyrophosphate analogues that include potent inhibitors of bone resorption, such as alendronate (4-amino-1-hydroxybutylidene-1,1-biphosphonic acid) (Sato et al. (1991) J. Clin. Invest. 88, 2095–2105).

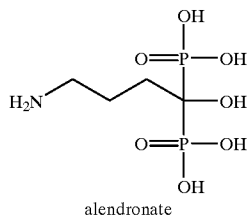

alendronate

The oral bioavailability of bisphosphonates (etidronate; clodronate; pamidronate; alendronate) in humans lies between 1% and 10% according to Lin (Bone 18, 75–85, 1996) and absorption is diminished when given with meals, especially in the presence of calcium. Therefore bisphosphonates should never be given at mealtime and never together with milk or diary products according to Fleisch (Bisphosphonates in bone disease, Stampli & Co., Bern 1993, p.50, and references cited therein).

The oral bioavailability of alendronate has been studied by Gertz et al. (Clinical Pharmacology & Therapeutics, vol. 58, pp. 288–298, 1995). It was found that taking alendronate either 60 or 30 minutes before breakfast reduced bioavailability by 40% relative to a 2-hour wait before a meal. Taking alendronate either concurrently with or 2 hours after breakfast drastically (>85%) impaired availability. A practical dosing recommendation, derived from these findings was that patients should take the drug with water after an overnight fast and at least 30 min before any other food or beverage.

Consequently, there is a need for pharmaceutical formulations comprising bisphosphonates, such as alendronate, which reduces the above mentioned drawbacks and allows the patient to take the medicament more conveniently, e.g. together with food intake.

Lipid Absorption Enhancers

The use of absorption enhancers of lipidic origin in pharmaceutical formulations is known in the art. For reviews, see e.g.:

van Hoogdalem et al., Pharmac. Theor., vol 44, 407–443 (1989);

Muranishi, Crit. Rev. Ther. Drug Carrier Syst., vol 7, 1–33 (1990);

Swenson and Curatolo, Adv. Drug Deliv. Rev., vol 8, 39–92 (1992);

Drug Absorption Enhancement (Ed.: A B G de Boer), Harwood Academic Publishers, 1994.

Specifically, medium chain glycerides have been studied and reported as absorption enhancers in a number of papers, see reference above and references therein. The main interest has been to utilize mixtures of mono-, di-, and triglycerides with 6 to 12 carbon atoms in the chains. More or less well defined samples of glycerides have been used, e.g. glyceryl mono-octanoate (Tramedico), Nikkol MGK (Nikko Chemicals), Sunsoft (Taiyo Kagaku), Imwitor (Hüls), Labrasol (Gattefosseé), and Labrafac Lipo (Gattefossé). Akoline MCM® (formerly called Capmul MCM) in a mono/diglyceride of medium chain fatty acids, primarily caprylic (n-octanoic) and capric (n-decanoic) acids.

Only a few reports deal with effects obtained when glycerides have been perorally administered (Sekine et al. (1985) J. Pharmacobio-Dyn. 8, 826; Beskid et al. (1988) Chemotherapy 34, 77).

Several other studies report results when liquid formulations of glycerides have been administered rectally (Matsumoto et al. (1989), Chem Pharm Bull. 37, 2477), or directly as solutions or emulsions by infusion or bolus into different parts of the small intestine (Constantinides et al. (1995) Pharm. Res. 12, 1561). The glycerides were used either as such, or in mixtures with dispersing agents like lecithins and surfactants to form aggregates like mixed micelles, microemulsions, dispersed lamellar phases etc, or to form self-emulsifying systems. A few patent publications have also disclosed the use of such glycerides in formulations, e.g. as components in microemulsions (WO 94/19003 and references therein), and in self-emulsifying systems with lecithins (WO 92/05771 and references therein).

Figure 1:
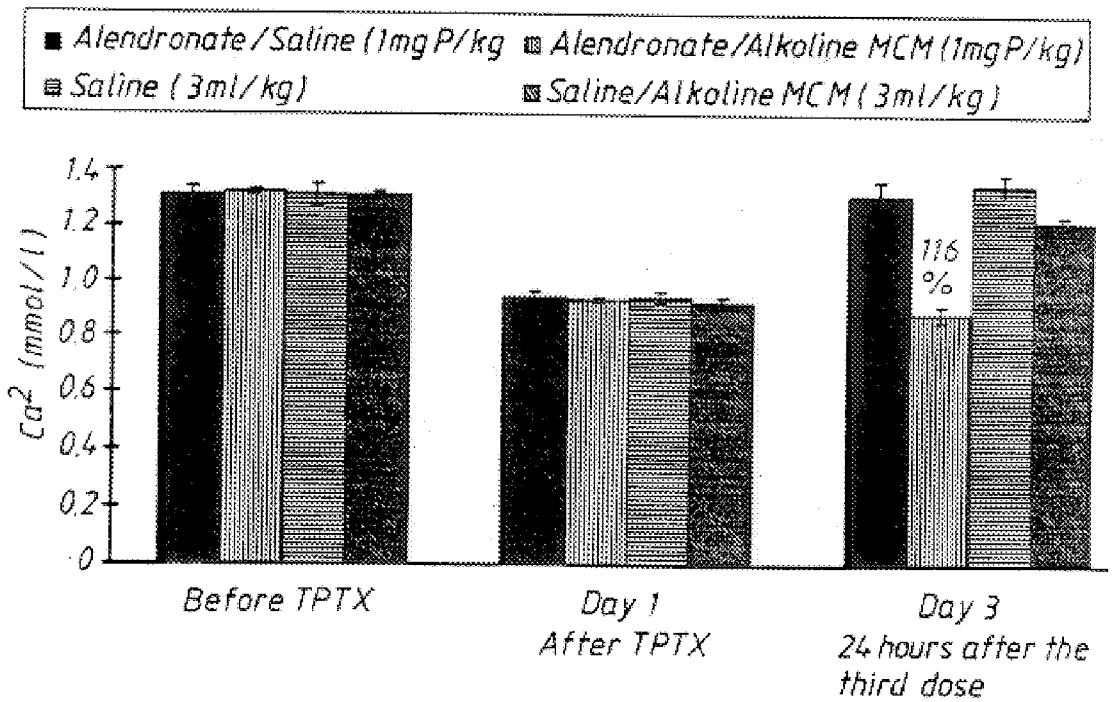
FIG. 1

Inhibitory effect of alendronate on bone resorption in a TPTX rat model.

FIG. 2

Dose-dependent effect of alendronate on bone resorption in a TPTX rat model.

(A) Alendronate/saline, intravenously (B) Alendronate/Akoline MCM®/saline, perorally (C) Alendronate/saline, perorally

DISCLOSURE OF THE INVENTION

It has surprisingly been found that the absorption of bisphosphonates can be modified by incorporating medium chain glycerides in pharmaceuticals formulations containing bisphosphonates. The use of medium chain glycerides as absorption enhancing agents will result in positive synergistic effects, such as enhanced and/or less variable absorption when bisphosphonates, e.g. alendronate, is given by different administration routes, such as the oral, the rectal, the buccal, the nasal and the pulmonary route.

Therefore, an object of the present is to provide a pharmaceutical formulation comprising at least one bisphosphonate and an absorption enhancing agent essentially consisting of a medium chain glyceride or a mixture of medium chain glycerides.

The said glyceride or glycerides has/have the formula I

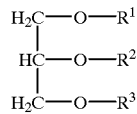

wherein $R^1$, $R^2$ and $R^3$ are the same or different and each represent a hydrogen atom or an alkanoyl chain having 6 to 18 carbon atoms, preferably 6 to 12 carbon atoms, provided that at least one of $R^1$, $R^2$ and $R^3$ is an alkanoyl group.

Preferably, at least one of $R^1$, $R^2$ and $R^3$ is hydrogen, i.e. the glyceride or glycerides is/are essentially monoglycerides and/or diglycerides.

When $R^1$, $R^2$ and/or $R^3$ represent an alkanoyl chain, the said alkanoyl chain has preferably 8 to 10 carbon atoms.

The absorption enhancing agent can e.g. be a commercially available composition of medium chain glycerides, such as Akoline MCM®. In another preferred form the invention thus provides a pharmaceutical formulation wherein the said absorption enhancing agent essentially is a mixture of medium chain monoglycerides and medium chain diglycerides, wherein the fatty acids are primarily caprylic (n-octanoic) and capric (n-decanoic) acids. In another preferred form the invention provides a pharmaceutical formulation wherein the absorption enhancing agent is selected from the group consisting of medium chain monoglycerides in the form of primarily caprylic and capric acids.

In another aspect of the invention provides a pharmaceutical formulation according to the above, in addition comprising not more than 20% water, buffer or saline, preferably 5% to 20% water, buffer or saline, and most preferably 10% water, buffer or saline. The solution should have a pH between 1 and 11. Preferably, a pH in the range 3 to 8.

In yet another aspect, the invention provides a pharmaceutical formulation according to above, in addition comprising 0.5% to 10%, preferably 1% to 5%, of a surface active ingredient, such as Tween® or Chremophore, preferably Tween-80®.

Preferably, the bisphosphonate has the general formula II

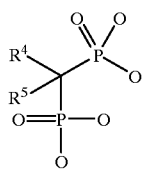

wherein
$R^4$ is H, OH or Cl; and
$R^5$ is
(a) alkyl with 1 to 6 carbon atoms, optionally substituted with amino, alkylamino, dialkylamino or heterocyclyl;
(b) halogen;
(c) arylthio, preferably chlorosubstituted;
(d) cycloalkylamino with 5 to 7 carbons; or
(e) saturated five or six membered nitrogen containing heterocyclyl with 1 or 2 heteroatoms.

Alkyl groups in alkylamino and dialkylamino may have 1 to 5 carbon atoms and may be combined independently in the dialkylamino group.

The term "heterocyclyl" means a saturated or unsaturated 5 to 7-membered heterocyclic group with one or two rings and 1 to 3 heteroatoms, independently chosen from N, O and S.

Unless otherwise stated or indicated, the term "aryl" denotes a substituted or unsubstituted phenyl, furyl, thienyl or pyridyl group, or a fused ring system of any of these groups, such as naphtyl.

The term "substituted" denotes an aryl group as defined above which is substituted by one or more alkyl, alkoxy, halogen, amino, thiol, nitro, hydroxy, acyl, aryl or cyano groups.

Compounds of the formula II include:
4-amino-1-hydroxybutylidene-1,1-bisphosphonic acid (alendronate),
N,N-dimethyl-3-amino-1-hydroxypropylidene-1,1-bisphosphonic acid (mildronate, olpadronate),
1-hydroxy-3-(N-methyl-N-pentylamino)propylidene-1,1-bisphosphonic acid (ibandronate),
1-hydroxy-2-(3-pyridyl)ethylidene-1,1-bisphosphonic acid (risedronate),
1-hydroxyethylidene-1,1-bisphosphonic acid (etidronate),
1-hydroxy-3-(1-pyrrolidinyl)propylidene-1,1-bisphosphonic acid,
1-hydroxy-2-(1-imidazolyl)etylidene-1,1-bisphosphonic acid (zoledronate),
1-hydroxy-2-(imidazo[1,2-a]pyridin-3-yl)ethylidene-1,1-bisphosphonic acid (minodronate),
1-(4-chlorophenylthio)methylidene-1,1-bisphosphonic acid (tiludronate),
1-(cycloheptylamino)methylidene-1,1-bisphosphonic acid (cimadronate, incadronate),
6-amino-1-hydroxyhexylidene-1,1-bisphosphonic acid (neridronate)
and pharmaceutically acceptable salts there of.

The most preferred compounds of the formula II are 4-amino-1-hydroxybutylidene-1,1-bisphosphonic acid (alendronate) and its pharmaceutically acceptable salts.

In a preferred form, the pharmaceutical formulation according to the invention is adapted for oral administration and may be given during fasted or fed conditions.

In the preparation of pharmaceutical formulations according to the invention in the form of dosage units for oral administration, the bisphosphonate and the absorption enhancing agent may be filled into soft or hard gelatin or cellulose capsules, mixed with solid, powdered ingredients, such as lactose, saccharose, sorbitol, mannitol, starch, amylopectin, cellulose derivatives, gelatin, or another suitable ingredient, as well as with disintegrating agents and lubricating agents such as magnesium stearate, calcium stearate, sodium stearyl fumarate and polyethylene glycol waxes. The mixture is then processed into granules or pressed into tablets.

The dosage form used may be a solid, semisolid or liquid preparation prepared by techniques which are known per se. Usually the active substance will constitute between 0.001% and 99% by weight of the preparation, preferably 0.003 to 1.3% by weight, most preferably 0.1 to 1%.

Suitable daily doses of bisphosphonates in therapeutic treatment of humans are about 0.001 to 100 mg/kg body weight at peroral administration, preferably 0.001 to 10 mg/kg, most preferably 0.005 to 0.3 mg/kg.

The enhancing agent, or the combination of enhancing agents, will constitute between 0.1 to 99.9% by weight of the preparation, preferably between 80% to 99.9% by weight.

The pharmaceutical formulations according to the invention are useful for inhibiting bone resorption and thus for the treatment or prevention of bone loss related to osteoporosis, age, steroid therapy, rheumatism, Paget's disease or cancer. The pharmaceutical formulations according to the invention are also useful for the treatment of hypercalcaemia.

Consequently, the use of the said pharmaceutical formulations for treating these conditions are additional aspects of the invention.

In another aspect the invention provides a process for the preparation of a pharmaceutical formulation according to the invention, said process comprising forming a mixture of (i) bisphosphonate, (ii) an absorption enhancing agent, and (iii) a pharmaceutically acceptable carrier.

In a further aspect the invention provides the use of bisphosphonate in conjunction with an absorption enhancing agent for the manufacture of a medicament for the inhibition of bone resorption, or thus for the treatment or prevention of bone loss related to osteoporosis, age, steroid therapy, rheumatism, Paget's disease or cancer, said absorption enhancing agent essentially consisting of a medium chain glyceride or a mixture of medium chain glycerides, optionally with 0.5 to 10%, surfactants added. Preferably, the said medicament is adapted for oral administration.

In yet a further aspect the invention provides a method for the inhibition of bone resorption, or thus for the treatment or prevention of bone loss related to osteoporosis, age, steroid therapy, rheumatism, Paget's disease or cancer, which method comprises administering to a mammal, including man, in need of such treatment an effective amount of a pharmaceutical formulation according to the invention. Preferably, the said pharmaceutical formulation is administered orally.

EXAMPLES

Example 1

Thyroparathyroidectomy (TPTX-rat model)

Female Sprague-Dawley rats from Molegaards Breeding Centre, Skensved, Denmark were used in the experiments. The animals were kept three by three in Macrolon cages, with free access to standard rat food pellets and tap water during the whole experiment. TPTX (Thyroparathyroidectomy) was preformed during anaesthesia with xylazine (Rompun®, 20 mg/ml, 0.25 ml/kg, intraperitoneally (i.p.)) and ketamine (Ketalar®, 50 mg/ml, 2.0 ml/kg, i.p.). After TPTX all rats were supplemented with 4 µg/kg thyroxin subcutaneously three times a week. TPTX adequacy was checked by determination of blood levels of $Ca^{2+}$ in a blood samples obtained from the vein of the tail 5–6 days after surgery. TPTX was considered successful if blood $Ca^{2+}$ was $\leq 80\%$ of the concentration found in the rats before surgery.

Bone resorption in the TPTX rats was stimulated by the arotinoid ethyl p-[(E)-2-(5,6,7,8-tetrahydro-5,5,8,8-tetramethyl-2-naphtyl)penyl]-benzoate (RO 13-6298, a gift from Hoffman-La Roche AG, Basel, Switzerland). RO 13-6298 was administered subcutaneously once daily (100 µg/kg in 1 ml/kg solved in polyethylene glycol 300 containing 10% ethanol) for three consecutive days (days 1, 2 and 3), day 1 being five to six days after TPTX.

Alendronate was dissolved in saline and/or suspended in Akoline MCM®/saline (9:1) Alendronate dissolved in saline was administered intravenously and orally, whereas alendronate suspended in Akoline MCM®/saline was administered orally. The drug was given on day 1, 2 and 3 together with RO 13-6298. Blood samples for determination of $Ca^{2+}$ were taken 24 hours after the third administration of alendronate.

Figure 2:
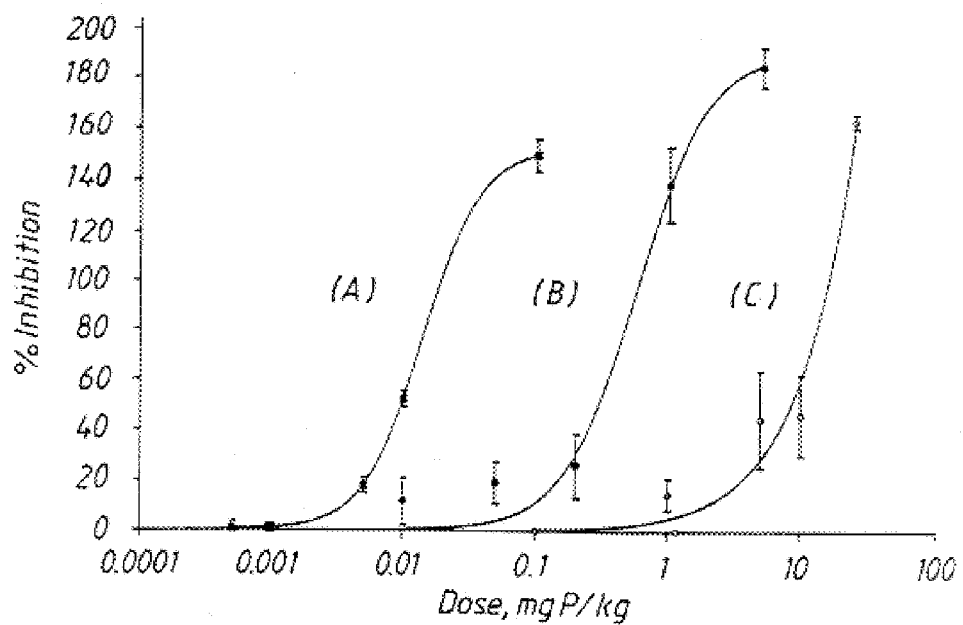

The inhibitory effect of alendronate was determined by measuring the increment in blood $Ca^{2+}$ on day 1, before administration of the first dose of alendronate, and the values obtained 24 hours after the third dose of alendronate (FIG. 1). The difference between the increment in the animals receiving just RO 13-6298 and those receiving RO 13-6298 and alendronate was then calculated and expressed as a percentage of the value obtained with RO 13-6298 alone (FIG. 2). An inhibition of 100% indicated that the blood $Ca^{2+}$ in the RO 13-6298 and alendronate treated animals was equal to the levels of blood $Ca^{2+}$ in the control group without RO 13-6298, meaning that RO 13-6298 induced effect was completely blocked.

The results shown in FIG. 1 indicate that, in the TPTX-rat model, there was no significant decrease of blood levels of $Ca^{2+}$ 24 hours after the third oral dose of alendronate (1 mgP/kg) dissolved in saline (0.9% NaCl) compared to the rats treated with only saline). When alendronate was suspended in Akoline MCM®/saline (9:1)(3 ml/kg) and given orally there was a significant decrease of plasma levels of $Ca^{2+}$ (116%) compared to the rats treated with only Akoline MCM®/saline. Consequently, there is an increased effect of alendronate in Akoline MCM®/saline compared to alendronate in saline given to rats with free access to food and tap water.

In the TPTX-rat model alendronate was administered in 0.01; 0.05; 0.2; 1 and 5 mgP/kg. As shown in FIG. 2, there was a dose-dependent decrease in blood levels of $Ca^{2+}$ after treatment with alendronate in saline i.v., alendronate in saline p.o. and alendronate in Akoline MCM®/saline (9:1). Regarding to the effect after i.v. administration, the bioavailability of alendronate in Akoline MCM®/saline calculated from effect data, was about 3% and alendronate in saline 0.1%, respectively. Thus, there was an approximately 30 times increase in bioavailability after oral administration if alendronate was suspended in Akoline MCM®/saline compared to saline.

Example 2

Examples of pharmaceutical formulations according to the invention:

Formulation A1

| Alendronate | 17 mg P |
|---|---|
| Akoline MCM ® | 9.0 g |
| 0.9% NaCl (saline) | 1.0 g |

Alendronate corresponding to approx. 17 mg of phosphorus was dissolved in 1.0 g of saline, pH adjusted to 3.8 and 9.0 g of Alkoline MCM® was added. The mixture was vortexed and dosed to the rats in a volume of 3 ml/kg and as described in Example 1, giving a dose of 5 mg P/kg. The results from this doing are shown in FIG. 1 and FIG. 2.

Formulation A2

| Alendronate | 3.5 mg P |
|---|---|
| Akoline MCM ® | 9.0 g |
| 0.9% NaCl (saline) | 1.0 g |

Alendronate corresponding to approx. 3.5 mg of phosphorus was dissolved in 1.0 g of saline, pH adjusted to 3.8 and Akoline MCM® 9.0 g was added and the mixture vortexed and dosed to rats in a volume of 3 ml/kg and as described in Example 1 giving a dose of approx. 1.0 mg P/kg. The results from this doing are shown in FIG. 1 and FIG. 2.

Formulation A3

| Alendronate | 0.7 mg P |
|---|---|
| Akoline MCM ® | 9.0 g |
| 0.9% NaCl (saline) | 1.0 g |

Alendronate corresponding to approx. 0.7 mg of phosphorus was dissolved in 1.0 g of saline, pH adjusted to 3.8 and Akoline MCM® 9.0 g was added and the mixture vortexed and dosed to rats in a volume of 3 ml/kg and as described in Example 1 giving a dose of approx. 0.2 mg P/kg. The results from this doing are shown in FIG. 1 and FIG. 2.

Formulation A4

| Alendronate | 0.2 mg P |
|---|---|
| Akoline MCM ® | 9.0 g |
| 0.9% NaCl (saline) | 1.0 g |

Alendronate corresponding to approx. 0.2 mg of phosphorus was dissolved in 1.0 g of saline, pH adjusted to 3.8 and Akoline MCM® 9.0 g was added and the mixture vortexed and dosed to rats in a volume of 3 ml/kg and as described in Example 1 giving a dose of approx. 0.05 mg P/kg. The results from this dosing are shown in FIG. 1 and FIG. 2.

Formulation A5

| Alendronate | 0.0.35 mg P |
|---|---|
| Akoline MCM ® | 9.0 g |
| 0.9% NaCl (saline) | 1.0 g |

Alendronate corresponding to approx. 0.035 mg of phosphorus was dissolved in 1.0 g of saline, pH adjusted to 3.8 and Akoline MCM® 9.0 g was added and the mixture vortexed and dosed to rats in a volume of 3 ml/kg and as described in Example 1 giving a dose of approx. 0.01 mg P/kg. The results from this doing are shown in FIG. 1 and FIG. 2.

Formulation B1

| Alendronate | 17 mg P |
|---|---|
| Akoline MCM ® | 9.0 g |
| Tween-80 | 0.3 g |
| 0.9% NaCl (saline) | 1.0 g |

Alendronate corresponding to approx 17 mg phosphorus was dissolved in the 3% Tween-80/1.0 g saline solution, pH adjusted to 3.8 and Akoline MCM® 9.0 g was added and the mixture vortexed and dosed to the rats as described for Formulation A1.

Formulation B2

| Alendronate | 3.5 mg P |
|---|---|
| Akoline MCM ® | 9.0 g |
| Tween-80 | 0.3 g |
| 0.9% NaCl (saline) | 1.0 g |

Alendronate corresponding to approx. 3.5 mg of phosphorus was dissolved in the 3% Tween-80/saline 1.0 g mixture, pH adjusted to 3.8 and Akoline MCM® 9.0 g was added and the mixture was vortexed and dosed to the rats as described Formulation A2

Formulation B3

| Alendronate | 0.7 mg P |
|---|---|
| Akoline MCM ® | 9.0 g |
| Tween-80 | 0.3 g |
| 0.9% NaCl (saline) | 1.0 g |

Alendronate corresponding to approx. 0.7 mg of phosphorus was dissolved in the 3% Tween-80/saline 1.0 g mixture, pH adjusted to 3.8 and Akoline MCM® 9.0 g was added and the mixture was vortexed and dosed to the rats as described Formulation A3

Formulation B4

| Alendronate | 0.2 mg P |
|---|---|
| Akoline MCM ® | 9.0 g |
| Tween-80 | 0.3 g |
| 0.9% NaCl (saline) | 1.0 g |

Alendronate corresponding to approx. 0.2 mg of phosphorus was dissolved in the 3% Tween-80/saline 1.0 g mixture, pH adjusted to 3.8 and Akoline MCM® 9.0 g was added and the mixture was vortexed and dosed to the rats as described Formulation A4

Formulation B5

| Alendronate | 0.035 mg P |
|---|---|
| Akoline MCM ® | 9.0 g |
| Tween-80 | 0.3 g |
| 0.9% NaCl (saline) | 1.0 g |

Alendronate corresponding to approx. 0.035 mg of phosphate was dissolved in the 3% Tween-80/saline 1.0 g mixture, pH adjusted to 3.8 and Akoline MCM® 9.0 g was added and the mixture was vortexed and dosed to the rats as described Formulation A5

Formulation C1–C5

| Alendronate | 0.035 to 17 mg P |
|---|---|
| Akoline MCM ® | 9.0 g |
| water | 1.0 g |

Each amount of alendronate corresponding to 0.035 to 17 mg phosphorus was dissolved in 1.0 g of water, pH adjusted to 3.8 and 9.0 g of Alkoline MCM® was added. The mixtures were vortexed and dosed to the rats as 3 ml/kg and as described for Formulations A1–A5.

Formulation D1–D5

| Alendronate | 0.035 to 17 mg P |
| Akoline MCM ® | 9.0 g |
| Tween-80 | 0.3 g |
| water | 1.0 g |

Each amount of alendonate corresponding to: 0.035 to 17 mg phosphorus was dissolved in 3% Tween-80/1.0 g water solution, pH adjusted to 3.8 and Akoline MCM® 9.0 g was added and the mixtures were vortexed and dosed to the rats as 3 ml/kg and as described for Formulations B1–B5.

Example 3

According to EXAMPLE 2, formulations A1–A5, B1–B5, C1–C5 and D1–D5, but with risedronate corresponding to 0.035 to 17 mg phosphorus.

Example 4

According to EXAMPLE 2, formulations A1–A5, B1–B5, C1–C5 and D1–D5, but with ibandronate corresponding to 0.02 to 15 mg phosphorus.

What is claimed is:

1. An oral dosage form comprising effective amounts of at least one bisphosphonate and an absorption enhancing agent, wherein the absorption enhancing agent enhances the bioavailability of the bisphosphonate and comprises a medium chain glyceride or a mixture of medium chain glycerides.

2. The oral dosage form according to claim 1, wherein the medium chain glyceride or glycerides has/have the formula I

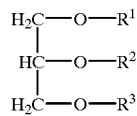

wherein $R^1$, $R^2$ and $R^3$ are the same or different and each represents a hydrogen atom or an alkanoyl chain having 6 to 18 carbon atoms, provided that at least one of $R^1$, $R^2$ and $R^3$ is an alkanoyl group.

3. The oral dosage form according to claim 2, wherein at least one of $R^1$, $R^2$ and $R^3$ is hydrogen.

4. The oral dosage form according to claim 2 or 3, wherein $R^1$, $R^2$ and $R^3$ represent hydrogen or an alkanoyl chain having 8 to 10 carbon atoms.

5. The oral dosage form according to claim 1, 2 or 3, wherein the absorption enhancing agent is essentially a mixture of medium chain monoglycerides and medium chain diglycerides.

6. The oral dosage form according to claim 1, wherein the bisphosphonate was the formula II

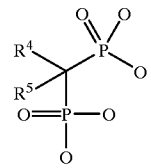

wherein
$R^4$ is H, OH or Cl, and
$R^5$ is
  (a) alkyl with 1 to 6 carbon atoms, optionally substituted with amino, alkylamino, dialkylamino or heterocyclyl;
  (b) halogen;
  (c) arylthio or chlorosubstituted arylthio;
  (d) cycloalkylamino with 5 to 7 carbons; or
  (e) saturated five or six membered nitrogen containing heterocyclyl with 1 or 2 heteroatoms.

7. The oral dosage form according to claim 6, wherein the bisphosphonate has the formula II
wherein
$R^4$ is H or OH and
$R^5$ is
  (a) alkyl with 1 to 6 carbon atoms, optionally substituted with amino, alkylamino, dialkylamino or heterocyclyl;
  (d) cycloalkylamino with 5 to 7 carbons; or
  (e) saturated five or six membered nitrogen containing heterocyclyl with 1 or 2 heteroatoms.

8. The oral dosage form according to claim 6, wherein the bisphosphonate has the formula II
wherein
$R^4$ is OH and
$R^5$ is
  (a) alkyl with 1 to 6 carbon atoms, optionally substituted with amino, alkylamino, dialkylamino or heterocyclyl;
  (d) cycloalkylamino with 5 to 7 carbons; or
  (e) saturated five or six membered nitrogen containing heterocyclyl with 1 or 2 heteroatoms.

9. The oral dosage form according to claim 6, wherein the bisphosphonate is selected from the group consisting of:
4-amino-1-hydroxybutylidene-1,1-bisphosphonic acid (alendronate);
N,N-dimethyl-3-amino-1-hydroxypropylidene-1,1-bisphosphonic acid (mildronate, olpadronate);
1-hydroxy-3-(N-methyl-N-pentylamino)propylidene-1,1-bisphosphonic acid (ibandronate);
1-hydroxy-2-(3-pyridyl)ethylidene-1,1-bisphosphonic acid (risedronate);
1-hydroxyethylidene-1,1-bisphosphonic acid (etidronate);
1-hydroxy-3-(1-pyrrolidinyl)propylidene-1,1-bisphosphonic acid;
1-hydroxy-2-(1-imidazolyl)etylidene-1,1-bisphosphonic acid (zoledronate);
1-hydroxy-2-(imidazo[1,2-a]pyridin-3-yl)ethylidene-1,1-bisphosphonic acid (minodronate);
1-(4-chlorophenylthio)methylidene-1,1-bisphosphonic acid (tiludronate);
1-(cycloheptylamino)methylidene-1,1-bisphosphonic acid (cimadronate, incadronate); and
6-amino-1-hydroxyhexylidene-1,1-bisphosphonic acid (neridronate),
and pharmaceutically acceptable salts thereof.

10. The oral dosage form according to claim 9, wherein the bisphosphonate is alendronate (4-amino-1- hydroxybutylidene-1,1-biphosphonic acid) or pharmaceutically acceptable salts thereof.

11. The oral dosage form according to claim 1, further comprising up to 20% of water, buffer or saline.

12. The oral dosage form according to claim 1, further comprising from 0.5% to 10% of a surface active ingredient.

13. A process for the preparation of an oral dosage form according to claim 1, comprising forming a mixture of (i) at least one bisphosphonate, (ii) an absorption enhancing agent, and (iii) a pharmaceutically acceptable carrier.

14. The oral dosage form according to claim 4, wherein the absorption enhancing agent is essentially a mixture of medium chain monoglycerides and medium chain diglycerides.

15. The oral dosage form according to claim 1, further comprising 5% to 20% of water, buffer or saline.

16. The oral dosage form according to claim 1, further comprising from 1% to 5% of a surface active ingredient.

17. The oral dosage form according to claim 1, wherein the bisphosphonate comprises 0.001% to 99% by weight of the dosage form.

18. The oral dosage form according to claim 1, wherein the bisphosphonate comprises 0.003% to 1.3% by weight of the dosage form.

19. The oral dosage form according to claim 1, wherein the bisphosphonate comprises 0.1% to 1% by weight of the dosage form.

20. The oral dosage form according to claim 1, wherein the enhancing agent or a combination thereof comprises 0.1% to 99.9% by weight of the dosage form.

21. The oral dosage form according to claim 1, wherein the enhancing agent or a combination thereof comprises 80% to 99.9% by weight of the dosage form.

22. The oral dosage form according to claim 4, wherein the fatty acids of the medium chain monoglycerides and medium chain diglycerides are primarily caprylic (n-octanoic) and capric (n-decanoic) acids.

23. The oral dosage form according to claim 5, wherein the fatty acids of the medium chain monoglycerides and medium chain diglycerides are primarily caprylic (n-octanoic) and capric (n-decanoic) acids.

24. A method for inhibiting bone resorption which comprises administering to a mammal in need of such treatment an oral dosage form according to any one of claims 1–3, 6–12, 14 or 15–21.

25. A method for the treatment and prevention of osteoporosis and bone loss related to age, steroid therapy, rheumatism, Paget's disease or cancer which comprises administering to a mammal in need of such treatment an oral dosage form according to any one of claims 1–3, 6–12, or 15–21.

26. The method of claim 24 or 25, wherein the mammal is a man.

27. The method according to claim 24 or 25, wherein the administered dose of the dosage form comprises the bisphosphonate within a range of 0.001 to 100 mg/kg body weight of the patient.

28. The method according to claim 24 or 25, wherein the administered dose of the dosage form comprises the bisphosphonate within a range of 0.001 to 10 mg/kg body weight of the patient.

29. The method according to claim 24 or 25, wherein the administered dose of the dosage form pharmaceutical formulation comprises the bisphosphonate within a range of 0.005 to 0.3 mg/kg body weight of the patient.

* * * * *